United States Patent [19]

Jaeger et al.

[11] 3,937,816
[45] Feb. 10, 1976

[54] GROWTH REGULATING COMPOSITIONS EXTRACTED FROM SPLEEN

[75] Inventors: Karl-Heinz Jaeger, Freiburg; Hellmut Mittenzwei, Munich, both of Germany

[73] Assignee: Solco Basel AG, Birsfelden, Switzerland

[22] Filed: Mar. 4, 1974

[21] Appl. No.: 447,939

Related U.S. Application Data

[63] Continuation of Ser. No. 64,033, July 21, 1970, abandoned, which is a continuation of Ser. No. 344,182, Feb. 12, 1964, abandoned, which is a continuation-in-part of Ser. No. 503,344, April 22, 1955, abandoned.

[52] U.S. Cl. .................................................. 424/95

[51] Int. Cl.² ........................................ A61K 35/28
[58] Field of Search .................................... 424/95

[56] References Cited
UNITED STATES PATENTS

| | | | |
|---|---|---|---|
| 2,239,345 | 4/1941 | Sperti | 424/95 |
| 2,662,047 | 12/1953 | Amozurrutia | 424/95 |

*Primary Examiner*—Sam Rosen
*Attorney, Agent, or Firm*—Hammond & Littell

[57] ABSTRACT

Compositions derived from spleens of vertebrata and process for obtaining the said compositions which are useful for increasing or decreasing the normal rate of tissue growth.

8 Claims, No Drawings

GROWTH REGULATING COMPOSITIONS EXTRACTED FROM SPLEEN

PRIOR APPLICATIONS

This application is a continuation of application Ser. No. 64,033 filed July 21, 1970, now abandoned, which in turn is a continuation of application Ser. No. 344,182 filed Feb. 12, 1964, now abandoned, which in turn is a continuation-in-part of application Ser. No. 503,344 filed Apr. 22, 1955, now abandoned.

The invention relates to novel growth regulating compositions derived from the spleen of vertebrata, especially warm blooded animals and to a novel process for the preparation of the said growth regulating compositions.

Tissue extracts which can be used therapeutically in the treatment of degenerative conditions, in cases of unsatisfactory cell regeneration, etc. are known. One way of preparing such extracts comprises wounding an animal by cutting, abrasion, penetrating or breaking the skin, cutting out the granulation tissue formed in the wounds after they have healed and extracting the granulation tissue. A variation of the process comprises cultivating on nutrient plasma the said granulation tissue and other kinds of connective tissue, injuring the resulting tissue cultures and extracting the said injured cultures.

Another modification of the known process comprises injecting the extracts of the granulation tissue into animals, withdrawing blood from the injected animals after a certain period of time and preparing a serum from the said blood. All these processes, however, are rather expensive and the yield of effective materials obtained thereby is quite small.

It is an object of the invention to provide novel growth regulating compositions derived from activated spleens.

It is another object of the invention to provide a novel, economical process for the preparation of growth regulating compositions derived from activated spleens.

It is a further object of the invention to provide a novel method of regulating the growth of tissues.

These and other objects and advantages of the invention will become obvious from the following detailed description.

The novel growth regulating compositions of the invention are protein-free extracts derived from spleens of vertebrata, especially warm blooded animals, which have been activated or stimulated by irradiation or by chemical stimulation and are in the form of aqueous solutions having 10 to 60 mg of solids per ml of solution. The composition gives a negative Heller's test and sulfosalicylic acid reaction and positive glucose oxydase reaction, Molish reaction, xanthoprotein reaction, Millon's reaction and ninhydrin reaction and has an absorption maximum in hydrochloric acid solution at 247 $\mu$. Paper chromatography shows the presence of the desoxy ribosides of adenine, uracil, cytosin, guanine and hypoxanthine and glutamic acid, asparagic acid, glycine, alanine, serine, valine and leucine.

The stimulation or the activation of the spleen of vertebrata may be effected either by administering to them one or more of the chemical compounds defined below or by subjecting the said spleens to irradiation. The amount of chemical stimulation or irradiation necessary to produce the desired effect can be easily determined by preliminary tests. The amounts of roentgen (R) needed to stimulate an organ (stimulating irradiation) is known and therefore it is possible to adjust the desired stimulation depending upon the type of irradiation. The dosages of the chemical treatment or of the irradiation should be below those dosages which cause irreparable damage to the organ and possible death of the vertebrata. These dosages are well known to those skilled in the art and can be obtained from many texts in this field.

Any type of irradiation is suitable which stimulates the spleen. Examples of suitable types are very short radium radiation, longwave, middlewave or shortwave X-ray radiation, grenz ray radiation (Bucky rays), ultraviolet light, infra-red, longwave heat radiation, corpuscular ray radiation such as by canal rays, rapidly moving electrons, positrons, neutrons and similar elementary particles or particles derived from radioactive isotopes. Ultrasonic waves may also be used for stimulation. Irradiation has the advantage that it is possible to focus most type of waves to the specific part of the body to be treated and to concentrate the said rays upon a specific plane of the animal's body.

The chemical stimulants are hypotonic aqueous solutions which are injected intravenously into the animal. Examples of suitable solvents are distilled water or hypotonic solutions whose ion concentrations may be between zero and a value which still causes hemolysis in the animal.

Examples of suitable chemical stimulants are salts which in aqueous solution form ions such as sodium chloride, sodium phosphate, sodium sulfate, other buffer compounds, dispersed substances which will not be removed in the urine but will be stored in the reticulo-endothelial system (RES) of the organism such as colloidal sulfur and india ink, dyestuffs particularly biologically active dyestuffs having a specific range of fluorescence such as methylene blue, eosine, trypan red, trypan blue, porphyrine, etc. and therapeutically active compounds such as ethyl palmitate, phenol derivatives, benzoic acid derivatives such as the methyl p-hydroxybenzoate, p-amino benzene and hemolytically active substances such as saponins and polyethylene glycol esters of fatty acids. Radioactive elements and compounds such as radioactive cobalt, iodine or phosphorus may also be used as chemical stimulants but are preferably used as indicators for the above-mentioned chemical stimulants.

The process of the invention for the preparation of growth regulating compositions derived from activated spleens comprises (1) stimulating the spleen of vertebrata by irradiation or intravenous injection of hypotonic solutions, (2) comminuting the spleen, (3) extracting the spleens with aqueous solutions, (4) removing proteins from the aqueous extract (5) neutralizing the protein-free solution and subjecting the solution to dialysis with a membrane adapted to pass compounds having a molecular weight up to 4500, (6) removing fatty materials from the inner dialysate and (7) concentrating the inner dialysate to a concentration of 10 to 60 mg of solids per ml.

The extraction of the spleen may be effected with water but an aqueous solution of lower alkanols such as ethanol and/or butanol is preferred since the deproteination step is preferably effected by precipitation from 85 % or higher alkanol solutions. The lower alkanols are easily removed after the deproteination by evaporation under vacuum at relatively low temperatures. Deproteination may also be effected by the addition of perchloric acid or trichloroacetic acid. The perchloric acid is removed by precipitation as potassium perchlorate which introduces inorganic ions in the solution of the final product. Fractionated deproteination with trichloroacetic acid gives somewhat lower yields since it is not as easily controlled as the use of lower alkanols.

The dialysis to decrease the amount of low molecular weight components having a weight below 4500 is preferably effected at low temperatures of the order of about 2°C. using water or dilute lower alkanols such as 10% aqueous ethanol as the dialysis media. Cellophane tubes have been found to be particularly suitable as the dialysing material although other dialysis materials may be used.

If necessary the pH of the inner dialysate is adjusted to about 7 and the solution is filtered to remove any salts that may precipitate. The solution is then concentrated under vacuum at temperatures not above 30°C., i.e. 20°–25°C. to a concentration of 10 to 60 mg of solids per ml of solution.

The removal of fatty material may be effected before or after the dialysis step and is effected by extraction with organic solvents such as ethyl ether to obtain clear aqueous solutions.

The concentrated solution obtained by concentration of the inner dialysate can be administered after sterile filtration topically, intramuscularly or transcutaneously. The spleen extracts are stable and may be stored for prolonged periods of time without suffering any loss of activity. However, if desired, a perservative such as phenol, cresol, etc. may be added. Preservatives to prevent a secondary infection of the solution after opening of the container in which it is supplied may also be added. The compositions of the invention are useful growth regulants. Growth regulation means that the spleen extract of the invention can increase or decrease the normal rate of growth of tissues depending upon the condition of the treated tissue. The spleen extract can enlarge the size of a spleen in a normal animal but if the spleen in the animal is enlarged, the administration of the spleen extract leads to a distinct reduction of the spleen hypertrophy.

The unique growth regulating properties of the spleen extract have been demonstrated on guinea pigs. Depending upon the original condition of connective tissue as discussed in the preceding paragraph, the same dose of the spleen extract of the invention accelerated cell growth in connective tissue poor in cells and inhibited cell growth in connective tissue rich in cells.

In the following examples there are described several preferred embodiments to illustrate the invention. However, it should be understood that the invention is not intended to be limited to the specific embodiments.

EXAMPLE I

Healthy young calves weighing about 60 kg received on the 14th, 12th and 10th day prior to slaughtering intravenous injections of 250 cc of a 0.01% aqueous india ink solution which amounted to 5% of the amount of circulating blood. After the animals were slaughtered, the organs showing visible accumulation of india ink in the reticulo endothelium such as the spleen and thymus were removed. The spleens of the calves showed under histologic examination a non-inflammatory hyper-plasia with a considerable reticulosis of the red pulpa and were about 50% heavier than the weight of spleens of untreated calves of the same age.

10 kg of the said spleens were frozen and ground through a finely perforated disc in a meat grinder. The finely ground spleen was admixed with 65 liters of 70% aqueous ethyl alcohol and the mixture was stirred for 2 hours at 0°C. After standing overnight at 0°C., the clear supernatant liquor was siphoned off and the residue was centrifuged. Although it is not always necessary, the extracted glands were again comminuted in the meat grinder and then were stirred for 2 hours with 40 liters of 60% aqueous ethyl alcohol at 0°C. After standing overnight at 0°C., the supernatant liquid was siphoned off and the residue was centrifuged. The comminuted spleens were extracted a third time in the same manner with 30 liters of 60% aqueous ethyl alcohol and the spleen residue was then discarded.

The three extracts were combined and then brought to a total concentration of 85% by volume of ethyl alcohol by the addition of 95 to 100% ethyl alcohol thereto which caused proteins to precipitate. The protein precipitate was removed by filtration and the clear filtrate was evaporated in a circulation evaporator to a final volume of 10 liters. 95 to 100% ethyl alcohol was added to the concentrated solution to readjust the ethyl alcohol content to 85% by volume. The solution was allowed to stand at 0°C. during which additional inactive proteins precipitated which were removed by filtration.

The resulting solution was again concentrated in vacuo to 10 liters and after cooling, the solution was shaken with 3 to 4 liters of ethyl ether to extract fatty material. The ether extract was separated and the concentration of the ethyl alcohol in the solution was again adjusted to 85% by volume. After filtering off the precipitated proteins, the clear solution was concentrated to a total volume of 5 liters, allowed to stand for several days at 0°C. and was then clarified by filtration through an asbestos filter. The resulting solution should be free from protein and if necessary the precipitation from 85% ethyl alcohol should be repeated.

The pH of the protein-free solution was adjusted to 7 and was dialyzed in a cellophane tube against an equal volume of a 10% aqueous ethyl alcohol solution. The outer dialysate was removed and the dialysis was repeated against the same volume of the 10% aqueous ethyl alcohol solution. The inner dialysate was then evaporated in vacuo to a concentration of 40 mgm of dry substance per milliliter. The clear yellowish aqueous solution was filtered under sterile conditions and filled into 5 cc ampules under sterile conditions.

The product had a negative reaction in Heller's test and the sulfosalicylic acid test showing the lack of proteins and exhibited a positive reaction in the glucose oxydase test, Molish test, xanthoprotein text, Millon's test and ninhydrin test. Its adsorption maximum in hydrochloric acid solution was at 247 $\mu$. Paper chromatography showed the presence of desoxyribosides of adenine, uracil, cytosine, guanine and hypoxanthine and glutamic acid, asparaginic acid, glycine, alanine, serine, valine and leucine. The dry product had an average molecular weight of 4500.

EXAMPLE II

An iodine containing X-ray agent was injected into a young calf for X-ray visualization of the spleen. As soon as the spleen became visible on the X-ray screen, the calf was narcotized and the spleen was laid open.

Several radium needles were applied thereto for 30 minutes and the wound was then sewed up. The calf's urine was then collected until the iodine was completely secreted from the spleen after which the animal was slaughtered. The spleen was removed, comminuted and extracted as in Example I to obtain a protein-free solution.

PHARMACOLOGICAL STUDY

I. Effect on mouse spleens:

The effect of the spleen extract produced by the process of Example I on mouse spleens was determined. In one test, the mice were injected once intravenously with 0.05 cc of the extract and the ATP-ase activity and weight of the mouse spleens were determined and compared with a control group of mice. In the second test, the test mice received a daily dose of 0.3 cc of the extract for 13 days after which the said comparisons were made. The results are summarized in Table I.

TABLE I

| Dosage | ATP-ase-Activity | Increase % over Controls | Weight of Spleen In mgm | Increase % over Controls |
| --- | --- | --- | --- | --- |
| Control Animals | 90.73 | 0 | 147.2 | 0 |
| Test Animals after 48 hours- one dose of 0.05 cc | 93.09 | 2.6 | 241.4 | 65.4 |
| Test Animals after 13 days- daily dose 0.3 cc | 99.15 | 6.5 | 275.4 | 87.1 |

The results of Table I show that an average weight increase of about 65% in the spleen is obtained after only 48 hours with a single injection and after 13 days an average weight increase of about 87% in the spleen is obtained. At the same time, the activity of ATP-degrading ferments increases only slightly so that a distinct reduction of the ATP-ase activity results.

Various modifications of the process of the invention may be made without departing from the spirit or scope thereof and it is to be understood that the invention is to be limited only as defined in the appended claims.

We claim:

1. A process for the preparation of compositions derived from spleens which comprises recovering the spleens of vertebrata selected from the group consisting of vertebrata whose spleen has been irradiated with a stimulating dose below the dose which irreparably damages the organ and vertebrata which have received intravenous injections of hypotonic aqueous solutions of a chemical stimulant, comminuting the said spleens, extracting the comminuted spleens with an aqueous solution, precipitating proteins from the aqueous extract by the addition thereto of a member selected from the group consisting of lower alkanols, perchloric acid and trichloroacetic acid, neutralizing the protein-free solution and subjecting it to dialysis with a membrane adapted to pass compounds having a molecular weight up to 4500, extracting fatty material from the resulting inner dialysate with a lower alkyl ether to obtain a clear aqueous solution and concentrating the resulting aqueous inner dialysate solution to a concentration of 10 to 60 mg of solid per milliliter of solution.

2. The process of claim 1 wherein the comminuted spleens are extracted with up to 70% aqueous ethyl alcohol.

3. The process of claim 1 wherein the proteins are removed by precipitation from at least 85% aqueous ethyl alcohol.

4. The process of claim 1 wherein the dialysis is effected against distilled water.

5. The process of claim 1 wherein the dialysis is effected against dilute aqueous ethyl alcohol.

6. An activated spleen extract produced by the process of claim 1

7. An extract of claim 6 wherein the vertebrata are calves.

8. A process for the preparation of compositions derived from spleens which comprises recovering the spleens of calves selected from the group consisting of calves whose spleens have been subjected to stimulating irradiation below the dose which irreparably damages the spleens and calves who have received the intravenous injections of hypotonic aqueous solutions of a chemical stimulant, comminuting the spleens, extracting the spleens with aqueous ethyl alcohol having a concentration up to 70%, precipitating proteins from the said extracts by adjusting the ethyl alcohol concentration to at least 85%, extracting the protein-free solutions with a lower alkyl ether to remove fatty substances, subjecting the resulting solution to dialysis with a cellophane membrane against an equal volume of a 10% aqueous ethyl alcohol solution and concentrating the inner dialysate to a concentration of 10 to 60 mg of solids per ml.

* * * * *